United States Patent
Choi

(10) Patent No.: US 10,022,072 B2
(45) Date of Patent: Jul. 17, 2018

(54) METHOD OF PROCESSING SIGNAL, METHOD OF RECOVERING SIGNAL, AND DEVICES PERFORMING THE METHODS

(71) Applicant: Samsung Electronics Co., Ltd., Suwon-si, Gyeonggi-do (KR)

(72) Inventor: Byung-Kwon Choi, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 9 days.

(21) Appl. No.: 15/093,181

(22) Filed: Apr. 7, 2016

(65) Prior Publication Data

US 2017/0112415 A1 Apr. 27, 2017

(30) Foreign Application Priority Data

Oct. 22, 2015 (KR) .................. 10-2015-0147291

(51) Int. Cl.
*A61B 5/11* (2006.01)
*A61B 5/00* (2006.01)
*G06K 9/00* (2006.01)

(52) U.S. Cl.
CPC ........... *A61B 5/112* (2013.01); *A61B 5/7232* (2013.01); *G06K 9/00335* (2013.01); *G06K 9/00523* (2013.01); *A61B 5/0002* (2013.01)

(58) Field of Classification Search
CPC .................. A61B 5/112; G06K 9/00
See application file for complete search history.

(56) References Cited

U.S. PATENT DOCUMENTS

| 6,958,045 B2 | 10/2005 | Takiguchi et al. |
| 2010/0176952 A1* | 7/2010 | Bajcsy ............. A61B 5/11 340/573.1 |
| 2014/0018705 A1 | 1/2014 | Wang et al. |
| 2015/0157525 A1* | 6/2015 | Choi ............. A61B 5/7232 700/245 |

FOREIGN PATENT DOCUMENTS

| JP | 4385274 B2 | 12/2009 |
| JP | 2012-008637 A | 1/2012 |
| KR | 10-1104591 B1 | 1/2012 |
| KR | 10-2013-0092849 A | 8/2013 |
| KR | 10-2014-0060737 A | 5/2014 |

OTHER PUBLICATIONS

Amit Pande et al.," Efficient Health Data Compression on Mobile Devices", Proceedings of the 3rd ACM MobiHoc workshop on Pervasive wireless healthcare, MobileHealth '13, Jan. 2013, pp. 1-0, XP055349198, New York, NY.
Extended European Search Report dated Mar. 17, 2017 for corresponding EP Application No. 16176126.7.
(Continued)

*Primary Examiner* — Jaison Joseph
(74) *Attorney, Agent, or Firm* — Harness, Dickey & Pierce, P.L.C.

(57) ABSTRACT

A signal processing method including receiving a signal, compressing the signal through a sampling of the signal, and generating transmission data of the signal by matching at least one feature indicating characteristics of the signal.

27 Claims, 12 Drawing Sheets

(56) References Cited

OTHER PUBLICATIONS

Han Su, et al., "*Human Gait Recognition Based on Motion Analysis*", *Proceedings of the Fourth International Conference on Machine Learning and Cybernetics*, Guangzhou, pp. 4464-4468, Aug. 2005, IEEE 2005.

Jani Mantyjarvi et al., "*Identifying users of portable devices from gait pattern with accelerometers*", *Vtt Electronics*, Oulu, Finland, IEEE 2005, pp. II-973-II-976.

Yi-Bo Li et al., "*Gait extraction and recognition based on lower leg and ankle*", *Shenyang Institute of Aeronautical Engineering*, Shenyang, China, IEEE 2010, pp. 379-382.

Zhenyu He et al., "*Activity Recognition from acceleration data Based on Discrete Consine Transform and SVM*," *School of Electronic & Information Engineering, South China University of Technology*, Guangzhou, China, IEEE 2009, pp. 5041-5044.

\* cited by examiner

Occurrence of distortion

METHOD OF PROCESSING SIGNAL, METHOD OF RECOVERING SIGNAL, AND DEVICES PERFORMING THE METHODS

CROSS-REFERENCE TO RELATED APPLICATION

This application claims under 35 U.S.C. § 119 to Korean Patent Application No. 10-2015-0147291, filed on Oct. 22, 2015, in the Korean Intellectual Property Office, the entire contents of which are incorporated herein by reference in its entirety.

BACKGROUND

1. Field

At least one example embodiment relates to a method of processing a signal, a method of recovering a signal, and/or devices performing the same.

2. Description of the Related Art

With the onset of societies providing health care services, a gait of a user may be used as a signal to track and observe a healthiness of the user. The gait signals may be stored and may be used for a personal health management and various fields of research.

To store the gait signals, signals related to joint angles may be stored at desired (or, alternatively, at preset) intervals.

SUMMARY

Some example embodiments relate to a signal processing method.

In some example embodiments, the signal processing method may include compressing a data signal to generate a compressed signal; and generating transmission data by matching at least one characteristic feature in the data signal and the compressed signal.

In some example embodiments, the signal processing method may further include determining the at least one characteristic feature within the data signal.

In some example embodiments, the at least one characteristic feature includes a start point, an end point, a peak point, and a valley point of the data signal.

In some example embodiments, the data signal indicates a movement of a user.

In some example embodiments, the at least one characteristic feature is based on a gait characteristic of the user.

In some example embodiments, the compressing includes sampling the data signal, and the method may further include appending sampling information associated with the sampling of the data signal to a header of the transmission data.

In some example embodiments, the compressing includes sampling the data signal to generate a sampled signal; and compressing the sampled signal based on a quantization parameter to generate the compressed signal.

In some example embodiments, the signal processing method may further include detecting the data signal at one or more intervals determined based on at least one step of a user associated with the data signal.

Some example embodiments relate to a signal recovering method.

In some example embodiments, the signal recovering method may include receiving transmission data from an external device; extracting, from the transmission data, a compressed signal having a data signal detected by the external device therein; and recovering the data signal based on the compressed signal and at least one characteristic feature of the data signal.

In some example embodiments, the recovering may include generating a sampling signal based on the compressed signal such that the sampling signal has a same period as the data signal; and performing compensation on the sampling signal based on the at least one characteristic feature.

In some example embodiments, the generating may include decompressing the compressed signal based on a quantization parameter to generate a decompressed signal; and sampling the decompressed signal based on sampling information included in the transmission data to generate the sampling signal.

In some example embodiments, the signal recovering method may further include extracting the at least one characteristic feature from the transmission data.

In some example embodiments, the signal recovering method may further include estimating the at least one characteristic feature based on the transmission data.

In some example embodiments, the at least one characteristic feature includes at least one of a start point, an end point, a peak point, and a valley point of the data signal.

In some example embodiments, the data signal indicates a movement of a user.

In some example embodiments, the at least one characteristic feature is based on a gait characteristic of the user.

Some example embodiments relate to a signal processing device.

In some example embodiments, the signal processing device may include a receiver configured to receive a data signal; and a controller configured to, compress the data signal to generate a compressed signal, and generate transmission data by matching at least one characteristic feature in the data signal and the compressed signal.

In some example embodiments, the controller is configured to determine the at least one characteristic feature within the data signal.

In some example embodiments, the at least one characteristic feature includes at least one of a start point, an end point, a peak point, and a valley point of the data signal.

In some example embodiments, the data signal indicates a movement of a user.

In some example embodiments, the at least one characteristic feature is based on a gait characteristic of the user.

In some example embodiments, the controller is configured to detect the data signal received by the receiver at one or more intervals determined based on at least one step of a user associated with the data signal.

Some example embodiments relate to a signal recovering device

In some example embodiments, the signal recovering device may include a receiver configured to receive transmission data from an external device; and a controller configured to, extract, from the transmission data, a compressed signal having a data signal detected by the external device therein, and recover the data signal based on the compressed signal and at least one characteristic feature of the data signal.

In some example embodiments, the controller is configured to, generate a sampling signal based on the compressed signal such that the sampling signal has a same period as the data signal, and perform compensation on the sampling signal based on at least one characteristic feature of the data signal.

In some example embodiments, the controller is configured to extract the at least one characteristic feature from the transmission data.

In some example embodiments, the controller is configured to estimate the at least one characteristic feature based on the transmission data.

In some example embodiments, the at least one the characteristic feature includes at least one of a start point, an end point, a peak point, and a valley point of the data signal.

In some example embodiments, the data signal indicates a movement of a user.

In some example embodiments, the at least one characteristic feature is based on a gait characteristic of the user.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
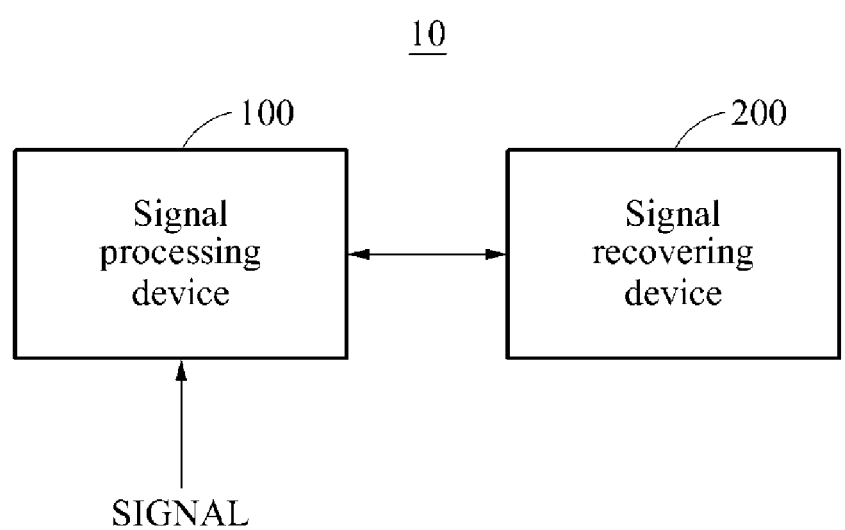
FIG. 1 illustrates an example of an electronic system according to example embodiments.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

The following specific structural or functional descriptions are exemplary to merely describe the examples, and the scope of the examples is not limited to the descriptions provided in the present specification.

It will be understood that, although the terms first, second, etc. may be used herein to describe various elements, these elements should not be limited by these terms. These terms are only used to distinguish one element from another. For example, a first signal could be termed a second signal, and, similarly, a second signal could be termed a first signal without departing from the teachings of the disclosure.

It will be understood that when an element or layer is referred to as being "on", "attached to", or "connected to" another element or layer, it can be directly on or connected to the other element or layer or through intervening elements or layers may be present. In contrast, when an element is referred to as being "directly on", "directly attached to", or "directly connected to" another element or layer, there are no intervening elements or layers present. Other words used to describe the relationship between elements or layers should be interpreted in a like fashion (e.g., "between" versus "directly between," "adjacent" versus "directly adjacent," "on" versus "directly on").

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "include/comprise" and/or "have" when used in this specification, specify the presence of stated features, integers, steps, operations, elements, components, and/or combinations thereof, but do not preclude the presence or addition of one or more other features, numbers, steps, operations, elements, components, and/or groups thereof.

Unless otherwise defined, all terms including technical and scientific terms used herein have the same meaning as commonly understood by one of ordinary skill in the art to which examples belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

FIG. 1 illustrates an electronic system according to example embodiments.

Referring to FIG. 1, an electronic system 10 may include a signal processing device 100 and a signal recovering device 200.

In some example embodiments, each of the signal processing device 100 and the signal recovering device 200 may be implemented as a stand-alone electronic system. In other example embodiments, the signal processing device 100 and the signal recovering device 200 may also be implemented as, for example, a personal computer (PC), a data server, and a portable electronic device.

The portable electronic device may be implemented as, for example a laptop computer, a mobile phone, a smart phone, a tablet PC, a mobile internet device (MID), a personal digital assistant (PDA), an enterprise digital assistant (EDA), a digital still camera, a digital video camera, a portable multimedia player (PMP), a personal navigation device or portable navigation device (PND), a handheld console, an e-book, and a smart device. The smart device may be implemented to be, for example, a smart watch and a smart band.

In other example embodiments, the signal processing device 100 and the signal recovering device 200 may be included in the aforementioned electronic device or communicate with one another through a communication interface.

In still other example embodiments, the signal processing device 100 and the signal recovering device 200 may be included in a motion assistance apparatus and/or an electronic device communicating with the motion assistance apparatus, or communicate with one another through a communication interface. The electronic device communicating with the motion assistance apparatus may include the aforementioned electronic device. Also, electronic device communicating with the motion assistance apparatus may include, for example, a wearable device and a remote controller configured to control an overall operation of the motion assistance apparatus.

The signal processing device 100 and the signal recovering device 200 may communicate with one another. For example, the signal processing device 100 and the signal recovering device 200 may exchange signals and/or data with one another.

The signal processing device 100 may receive signals sensed by one or more sensors. The signals sensed by the sensors may also be referred to as, for example, SIGNAL throughout the present disclosure and the drawings. In an example, the sensors may be implemented in the signal processing device 100. Alternatively, the sensors may be external devices implemented externally to the signal processing device 100 separately.

The signal processing device 100 may process the SIGNAL, and generate transmission data associated with the SIGNAL based on at least one feature indicating characteristics of the SIGNAL and a processed signal obtained though the processing. The signal processing device 100 may transmit the transmission data to the signal recovering device 200.

The signal recovering device 200 may receive the transmission data from an external device, for example, the signal processing device 100. The signal recovering device 200 may extract a signal into which the SIGNAL is compressed from the transmission data, and recover the SIGNAL based on the extracted signal and at least one feature indicating characteristics of the SIGNAL.

In an example, the SIGNAL may be one or more biosignals. The biosignals may indicate any type of signal measured, monitored, or sensed with respect to a biological being based on a continual, intermittent, or one-time method, and may be unique for each biological being. The biosignal may include, for example, an electrocardiogram (ECG) signal, a photoplethysmogram (PPG) signal, an electromyogram (EMG) signal, a voice, and an impedance signal generated in a body.

In another example, the SIGNAL may be one or more gait signals. The gait signal may be a signal sensed based on a movement of a user that triggers the SIGNAL. The gait signal may include information associated with joints of the user performing a pathological gait or an abnormal gait.

The gait signal may include angular information associated with at least one of, for example, a hip-joint, a knee-joint, and an ankle-joint of the user. Also, the gait signal may include acceleration information of the user performing the gait. The acceleration information may include at least one of X-axial, Y-axial, and Z-axial accelerations or X-axial, Y-axial, and Z-axial angular velocities based on a gait motion.

Concisely, the gait signal may indicate any and all signals of the user sensed based on the gait motion of the user.

The signal processing device 100 may efficiently generate compressed data associated with the SIGNAL based on the signal into which the SIGNAL is compressed and the at least one feature indicating the characteristics of the SIGNAL. The signal recovering device 200 may compensate for a distortion due to the compressing based on the at least one feature indicating the characteristics of the SIGNAL, thereby recovering the SIGNAL from the compressed data.

Figure 2:
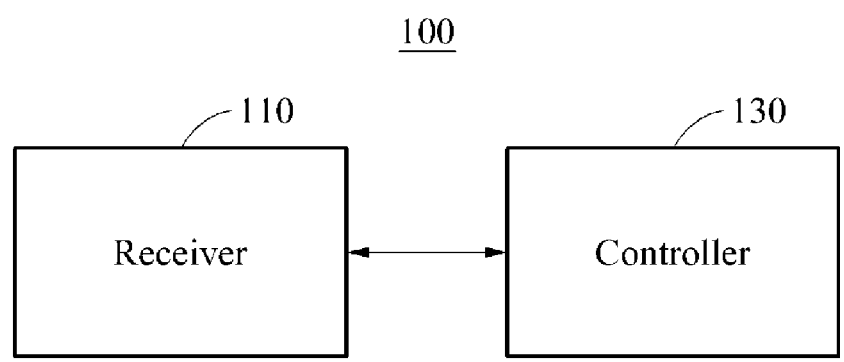
FIG. 2 illustrates an example of a signal processing device according to example embodiments.
Figure 3:
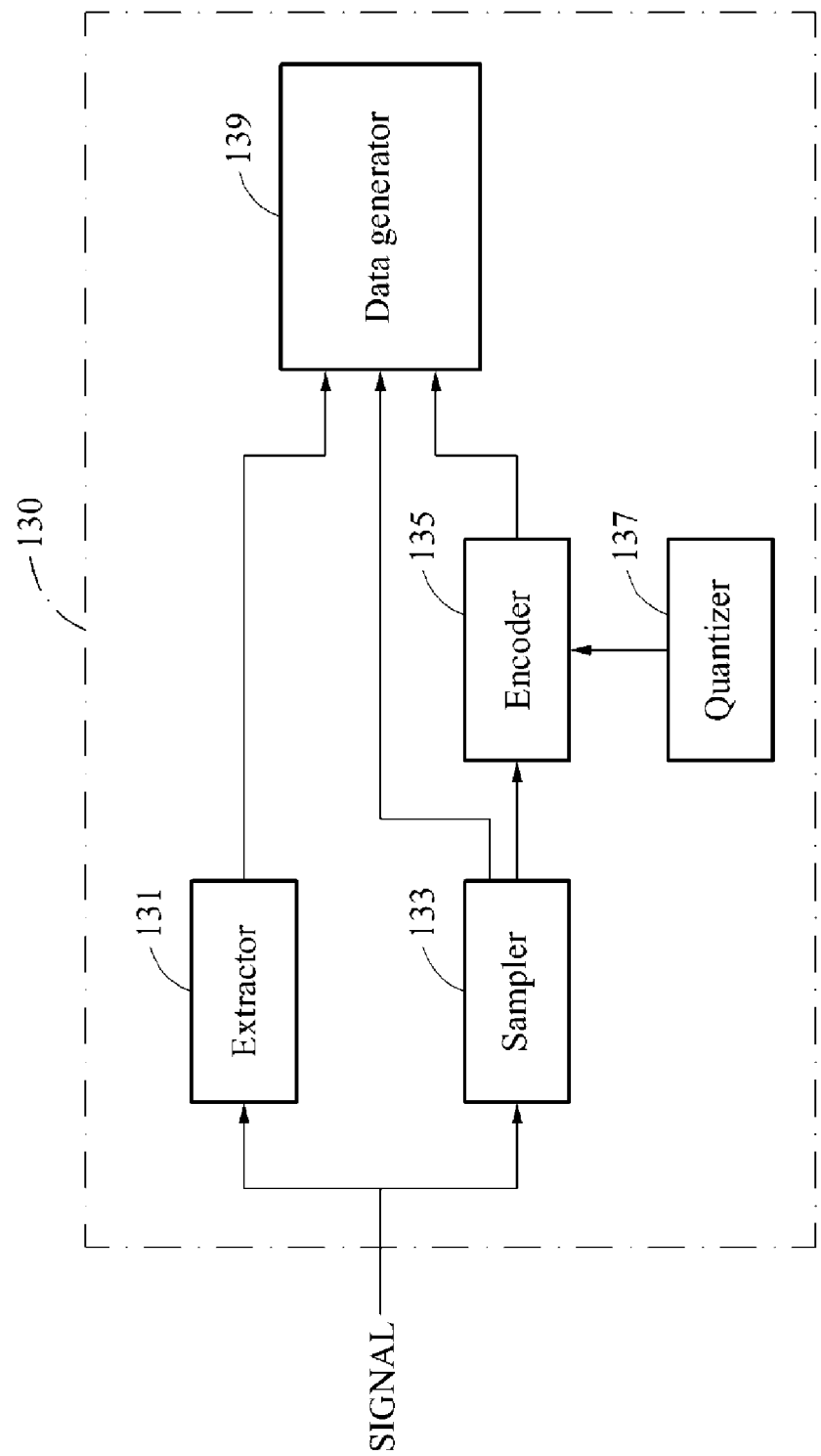
FIG. 3 illustrates an example of a controller included in a signal processing device according to example embodiments.
Figure 4:
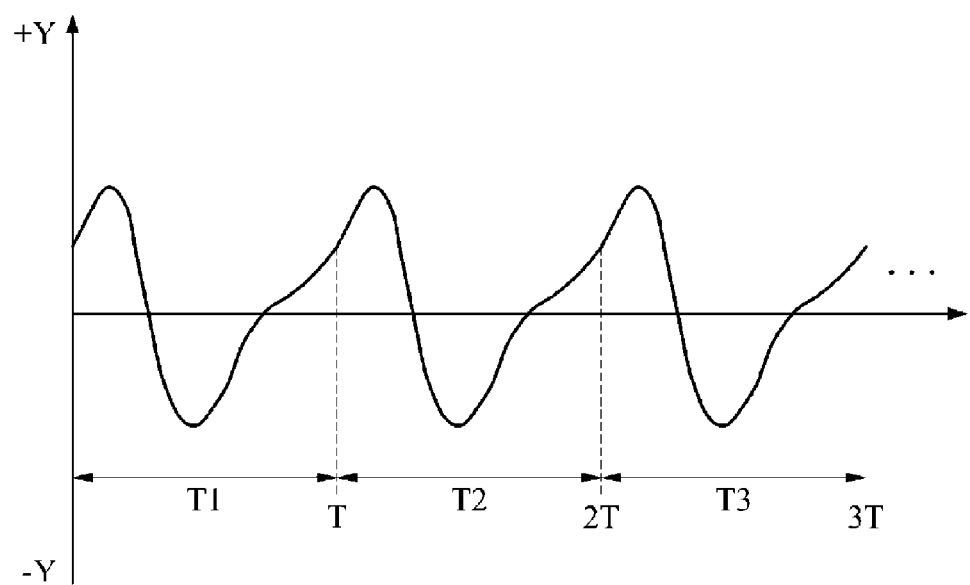
FIG. 4 illustrates an example of a signal detected by the signal processing device of FIG. 1.

FIG. 2 illustrates a signal processing device according to example embodiments. FIG. 3 illustrates a controller included in a signal processing device according to example embodiments. FIG. 4 illustrates an example of a signal detected by the signal processing device 100 of FIG. 1.

Referring to FIGS. 1 through 4, the signal processing device 100 may include a receiver 110 and a controller 130.

The receiver 110 may receive SIGNAL from a sensor. The receiver 110 may include a communication interface to receive the SIGNAL from the sensor.

The communication interface may include wireless Internet interfaces, such as a wireless local area network (WLAN) interface, a wireless fidelity (Wi-Fi) interface, a digital living network alliance (DLNA) interface, a wireless broadband (WiBro) interface, a world interoperability for microwave access (WiMAX) interface, and a high-speed downlink packet access (HSDPA) interface, for example. Additionally, the communication interface may include short-range communication interfaces, such as a Bluetooth interface, radio frequency identification (RFID) interface, infrared data association (IrDA) interface, an ultra wideband (UWB) interface, a ZigBee interface, and a near field communication (NFC) interface, for example. Also, the communication interface may include any type of communication interface, for example, a wired communication interface, to perform a communication with an external source.

The receiver 110 may detect the SIGNAL at intervals of a desired (or, alternatively, a predetermined) period. As illustrated in FIG. 4, the SIGNAL may be detected at intervals of a period of time and segmented into intervals T1, T2, and T3. In a graph of FIG. 4, an X axis represents a time or a period, and a Y axis represents an intensity of the SIGNAL. The Y axis may also represent a value of, for example, a voltage, a current, and an angle.

The SIGNAL may be, for example, a gait signal sensed based on a movement of a user that triggers the SIGNAL. In this example, the gait signal may have a characteristic that a pattern is repeated based on a gait characteristic at intervals of a desired (or, alternatively, a predetermined) period. The desired (or, alternatively, the predetermined) period may be determined based on at least one step of the user that triggers the SIGNAL. For example, the desired (or, alternatively, the predetermined) period may be determined based on a basic unit of a gait, a step or a stride. The step may be classified based on a single heel strike. The heel strike may indicate a state in which a sole of a foot is in contact with a ground. The stride may be defined based on, for example, two steps.

The controller 130 may sample the SIGNAL to generate a sampled signal and compress the sampled signal obtained through the sampling. Also, the controller 130 may generate transmission data of the SIGNAL by matching the compressed signal and at least one feature indicating characteristics of the SIGNAL.

The controller 130 may include a processor and a memory (not shown).

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor may be implemented by at least one semiconductor chip disposed on a printed circuit board. The processor may be an arithmetic logic unit, a digital signal processor, a microcomputer, a field programmable array, a programmable logic unit, a microprocessor or any other device capable of responding to and executing instructions in a defined manner.

The processor may be programmed with instructions that configure the processor into a special purpose computer to perform the operations of an extractor 131, a sampler; 133, an encoder 135, a quantizer 137, and a data generator 139. For example, when programmed, the processor may improve the functioning of the signal processing device 100 itself by efficiently compressing a gait signal SIGNAL based on characteristics of the gait signal SIGNAL.

The extractor 131 may extract the at least one feature indicating the characteristics of the SIGNAL based on the SIGNAL. For example, the at least one feature may include at least one of a start point, an end point, a peak point, and a valley point of the SIGNAL. The peak point may be, for example, a point representing a maximum value and the valley point may be, for example, a point representing a minimum value.

When the SIGNAL is the gait signal sensed based on the movement of the user that triggers the SIGNAL, the at least one feature indicating the characteristics of the SIGNAL may be based on a gait characteristic of the user. Location information and/or time information of at least one of the start point, the end point, the peak point, and the valley point may be determined based on the gait characteristic of the user.

The extractor 131 may extract the at least one feature from the SIGNAL at desired (or, alternatively a predetermined) time intervals spaced a sampling period apart. As an example, the extractor 131 may extract at least one of the start point, the end point, the peak point, and the valley point of the SIGNAL detected in the interval T1. The extractor 131 may extract at least one of the start point, the end point, the peak point, and the valley point of the SIGNAL detected in the interval T2. The extractor 131 may extract at least one of the start point, the end point, the peak point, and the valley point of the SIGNAL detected in the interval T3.

The extractor 131 may transmit at least one extracted feature of the SIGNAL to the data generator 139.

The sampler 133 may sample the SIGNAL. For example, the sampler 133 may sample the SIGNAL detected at the time intervals.

The sampler 133 may transmit a sampled signal obtained by sampling the SIGNAL to the encoder 135. Also, the sampler 133 may transmit sampling information of the SIGNAL to the data generator 139. The sampling information may include, for example, at least one of an original period and a sampling period of the SIGNAL.

The encoder 135 may encode the sampled signal. For example, the encoder 135 may compress the sampled signal based on a quantization parameter. Concisely, the encoder 135 may compress the sampled signal based on a compression method. The compression method may include various compression methods, for example, a discrete cosine transform (DCT), a wavelet transform (WT), and a fast Fourier transform (FFT) but not limited thereto.

The encoder 135 may transmit the encoded signal, for example, the compressed signal to the data generator 139.

The quantizer 137 may determine the quantization parameter based on at least one of a compression rate and an accuracy of the SIGNAL. For example, the compression rate and the accuracy may be set based on the SIGNAL. The quantizer 137 may transmit the quantization parameter to the encoder 135.

The data generator 139 may generate the transmission data of the SIGNAL by matching the compressed signal and at least one feature indicating characteristics of the SIGNAL. In this example, a header of the transmission data may include the sampling information of the SIGNAL.

The data generator 139 may transmit the transmission data of the SIGNAL to the signal recovering device 200.

Figure 5:
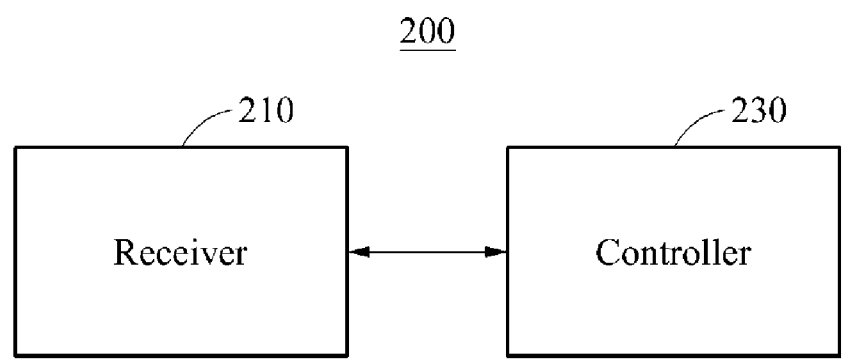
FIG. 5 illustrates an example of a signal recovering device according to example embodiments.

FIG. 5 illustrates a signal recovering device according to example embodiments.

Referring to FIGS. 1 and 5, the signal recovering device 200 may include a receiver 210 and a controller 230.

The receiver 210 may receive transmission data of SIGNAL from an external device, for example, the signal processing device 100. The receiver 210 may include a communication interface to receive the transmission data.

The communication interface may include wireless Internet interfaces, such as a WLAN interface, a Wi-Fi interface, a DLNA interface, a WiBro interface, a WiMAX interface, and an HSDPA interface, for example. Additionally, the communication interface may include short-range communication interfaces, such as a Bluetooth interface, RFID interface, IrDA interface, a UWB interface, a ZigBee interface, and an NFC interface, for example. Also, the communication interface may include any type of communication interface, for example, a wired communication interface, to perform a communication with an external source.

The controller 230 may extract, from the transmission data, a signal having the SIGNAL compressed therein, and recover the SIGNAL based on the extracted signal and at least one feature indicating characteristics of the SIGNAL.

Figure 6:
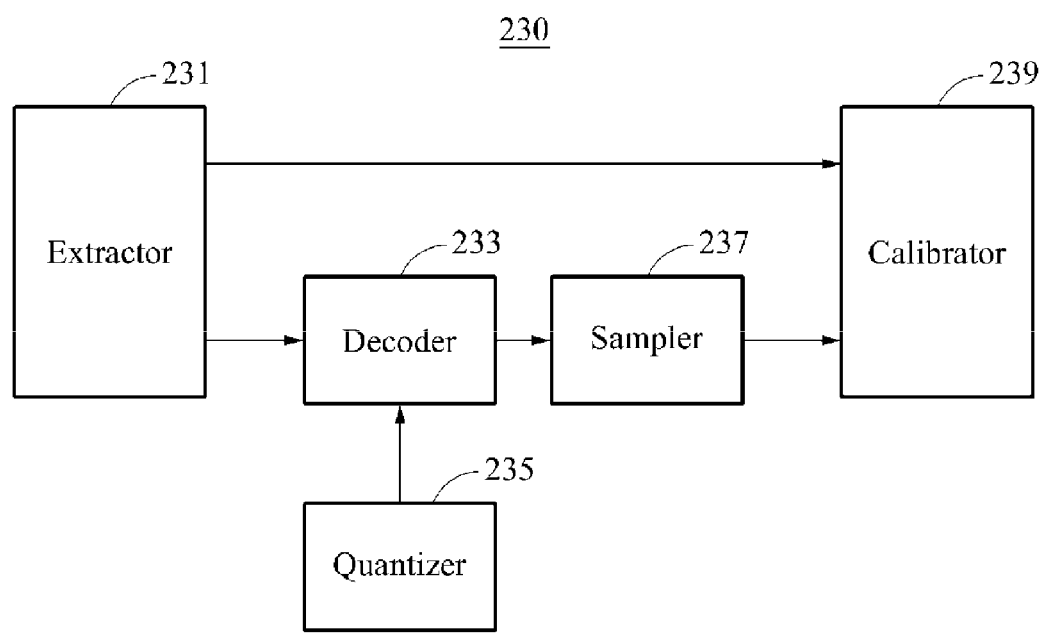
FIG. 6 illustrates an example of a controller included in a signal recovering device according to example embodiments.

FIG. 6 illustrates an example of a controller included in a signal recovery device according to example embodiments.

Referring to FIGS. 1, 5, and 6, the controller 230 may include a processor and a memory (not shown).

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor may be implemented by at least one semiconductor chip disposed on a printed circuit board. The processor may be an arithmetic logic unit, a digital signal processor, a microcomputer, a field programmable array, a programmable logic unit, a microprocessor or any other device capable of responding to and executing instructions in a defined manner.

The processor may be programmed with instructions that configure the processor into a special purpose computer to perform the operations of an extractor 231, a decoder 233, a quantizer 235, a sampler 237, and a calibrator 239. For example, when programmed, the processor may improve the functioning of the signal recovering device 200 itself by efficiently recovering the gait signal SIGNAL from compression data by compensating for a compression distortion based on the characteristics of the original gait signal SIGNAL.

The extractor 231 may extract, from the transmission data, a signal having SIGNAL compressed therein. Also, the extractor 231 may extract, from the transmission data, at least one feature indicating characteristics of the SIGNAL.

The extractor 231 may transmit the extracted signal to the decoder 233, and transmit the at least one feature to the calibrator 239.

The decoder 233 may decode the extracted signal. For example, the decoder 233 may decompress the extracted signal based on a quantization parameter. Concisely, the decoder 233 may decompress the extracted signal based on a decompression method. The decompression method may include various decompression methods, for example, an inverse discrete cosine transform (IDCT), an inverse wavelet transform (IWT), an inverse fast Fourier transform (IFFT) but not limited thereto.

The quantizer 235 may set the quantization parameter based on at least one of a decompression rate and an accuracy of the SIGNAL. For example, the accuracy and the decompression rate may be set based on the SIGNAL. The quantizer 235 may transmit the quantization parameter to the decoder 233.

The sampler 237 may generate a sampling signal based on the decompressed signal. For example, the sampler 237 may generate a sampling signal having an original period of the SIGNAL by sampling the decompressed signal based on sampling information included in a header of the transmission data. The sampler 237 may transmit the sampling signal to the calibrator 239.

The calibrator 239 may calibrate the sampling signal based on the at least one feature indicating the characteristics of the SIGNAL. Thus, the calibrator 239 may recover the SIGNAL based on the at least one feature.

Figure 7:
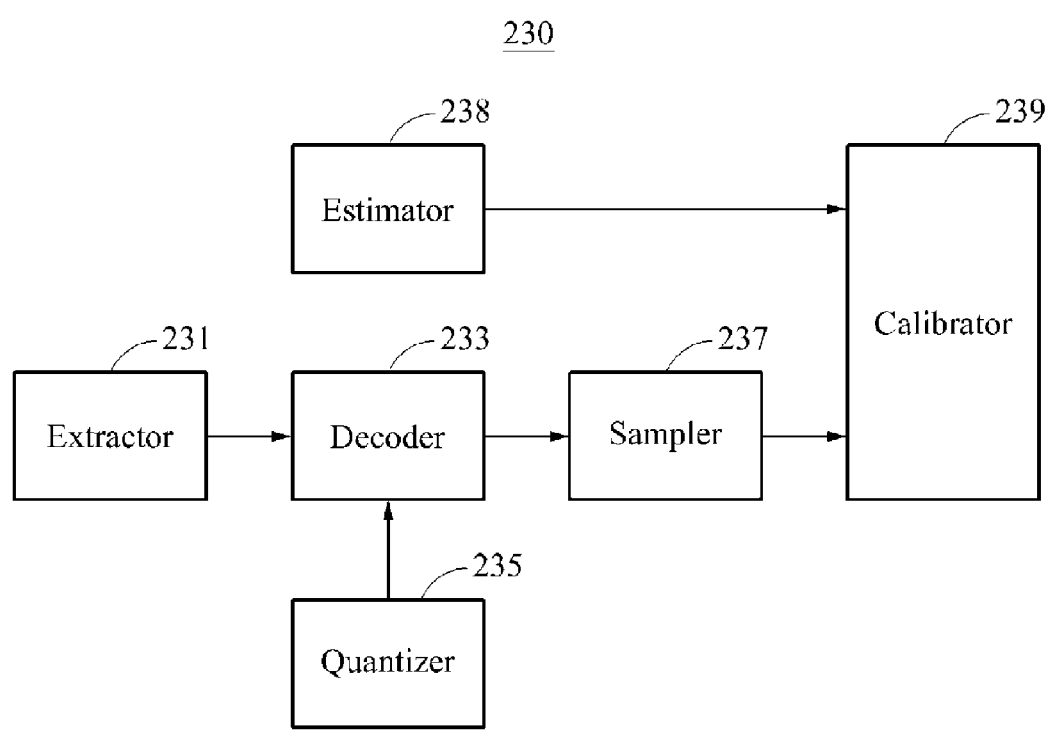
FIG. 7 illustrates another example of a controller included in a signal recovering device according to example embodiments.

FIG. 7 illustrates another example of a controller included in a signal recovery device according to example embodiments.

Referring to FIGS. 1, 5, and 7, the processor (not shown) of the controller 230 may be programmed with instructions that configure the processor into a special purpose computer to perform the operations of the extractor 231, the decoder 233, the quantizer 235, the sampler 237, an estimator 238, and the calibrator 239. Thus, in an example of FIG. 7, the controller 230 may further be configured to perform the operations of the estimator 238.

The estimator 238 may estimate at least one feature indicating characteristics of SIGNAL. For example, the at least one feature may include at least one of a start point, an end point, a peak point, and a valley point of the SIGNAL. The peak point may be, for example, a point representing a maximum value and the valley point may be, for example, a point representing a minimum value. In this example, the extractor 231 may not need to extract the at least one feature indicating the characteristics of the SIGNAL from transmission data.

As an example, when the SIGNAL includes a gait signal sensed based on a movement of a user that triggers the SIGNAL, the estimator 238 may estimate the at least one feature indicating the characteristics of the SIGNAL based on a gait characteristic of the user. The estimator 238 may estimate at least one of the start point, the end point, the peak point, and the valley point of the SIGNAL.

The estimator 238 may transmit at least one estimated feature to the calibrator 239.

Configurations and operations of how the controller 230 performs the operations of the extractor 231, the decoder 233, the sampler 235, the quantizer 237, and the calibrator 239 described in an example of FIG. 7 may be subsequently the same as configurations and operations of how the controller 230 performs the operations of the extractor 231, the decoder 233, the sampler 235, the quantizer 237, and the calibrator 239 described in an example of FIG. 6. Thus, repeated descriptions with respect to the extractor 231, the decoder 233, the sampler 235, the quantizer 237, and the calibrator 239 of FIG. 7 will be omitted for increased clarity and conciseness.

Figure 8:
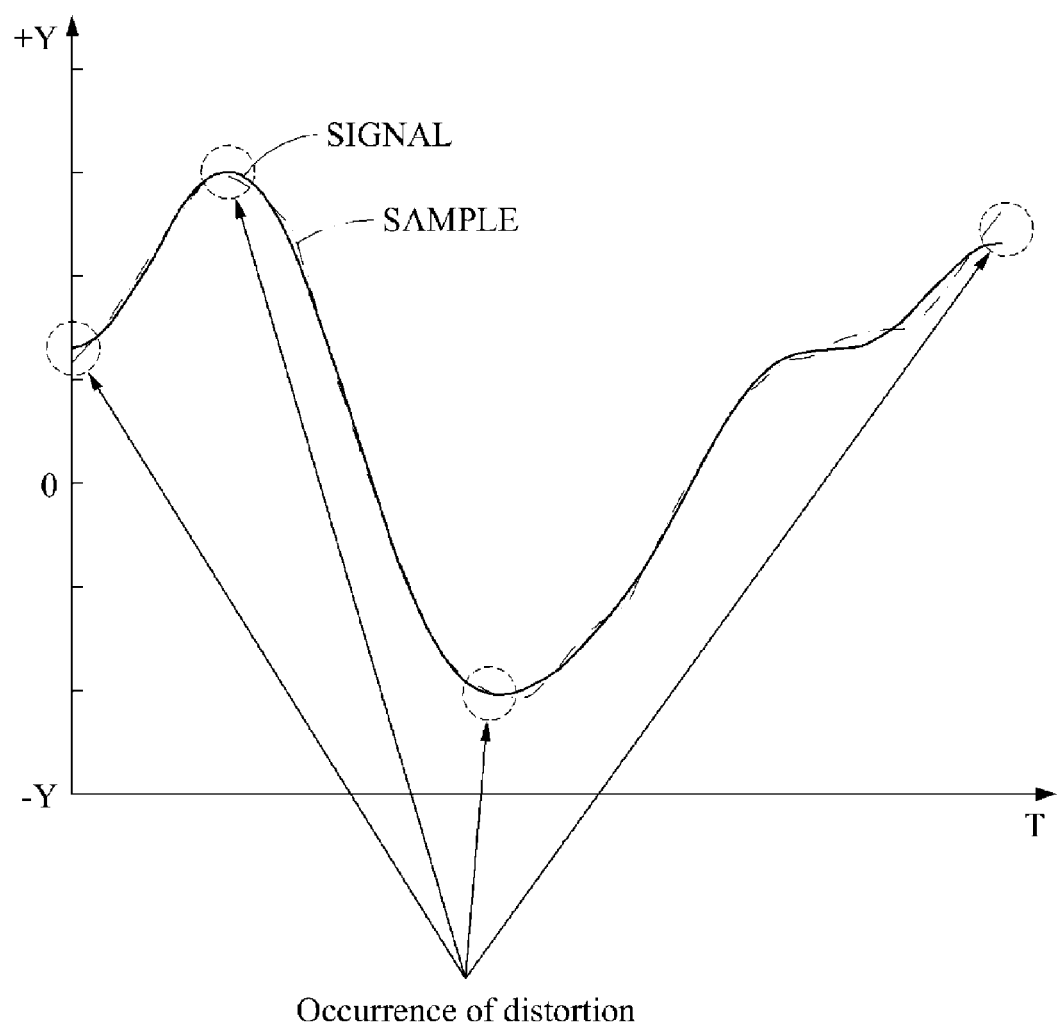
FIG. 8 illustrates an example of a signal recovered by the signal recovering device of FIG. 1.

FIG. 8 illustrates an example of a signal recovered by a signal recovering device according to example embodiments.

In a graph of FIG. 8, an X axis represents a time or a period, and a Y axis represents an intensity of a signal. The Y axis may also represent a value of, for example, a voltage, a current, and an angle.

Referring to FIG. 8, a sampling signal having an original period of SIGNAL through the decoder 233 and the sampler 235 may correspond to the SIGNAL. The sampling signal having an original period of SIGNAL may also be referred to, for example, SAMPLE throughout the present disclosure and the drawings. For example, at least one feature indicating characteristics of the SAMPLE may correspond to at least one feature indicating characteristics of the SIGNAL.

The at least one feature indicating the characteristics of the SAMPLE may include at least one of a start point, an end point, a peak point, and a valley point of the SAMPLE. The peak point may be, for example, a point representing a maximum value and the valley point may be, for example, a point representing a minimum value.

As illustrated in FIG. 8, a distortion may occur at a point corresponding to the at least one feature indicating the characteristics of the SIGNAL, of the SAMPLE. The distortion may occur in a process in which the SIGNAL is compressed by the encoder 135 of the signal processing device 100.

Thus, the calibrator 239 may recover the SIGNAL by calibrating the SAMPLE based on the at least one feature indicating the characteristics of the SIGNAL.

Figure 9:
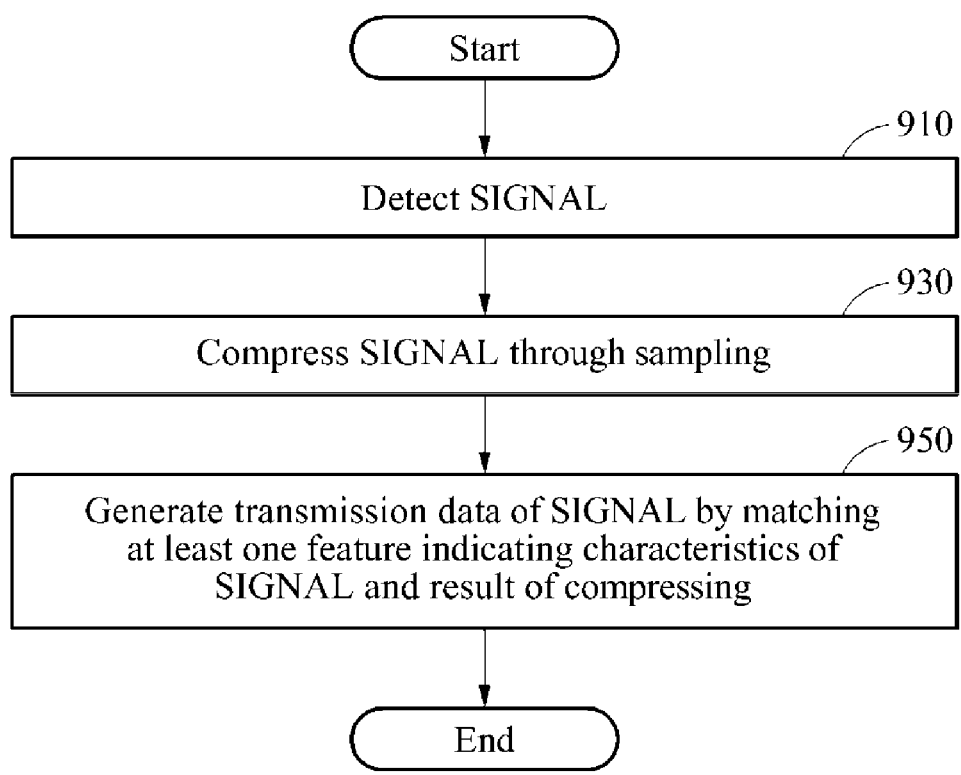
FIG. 9 illustrates an example of a signal processing method according to example embodiments.

FIG. 9 illustrates an example of a signal processing method according to example embodiments.

Referring to FIG. 9, in operation 910, the receiver 110 of the signal processing device 100 may detect the signal SIGNAL. For example, the receiver 110 may detect the SIGNAL at desired (or, alternatively, a predetermined) intervals or periods.

In operation 930, the controller 130 may compress the SIGNAL through a sampling of the SIGNAL.

In operation 950, the controller 130 may generate transmission data of the SIGNAL by matching at least one feature indicating characteristics of the SIGNAL and a result of the compressing.

Figure 10:
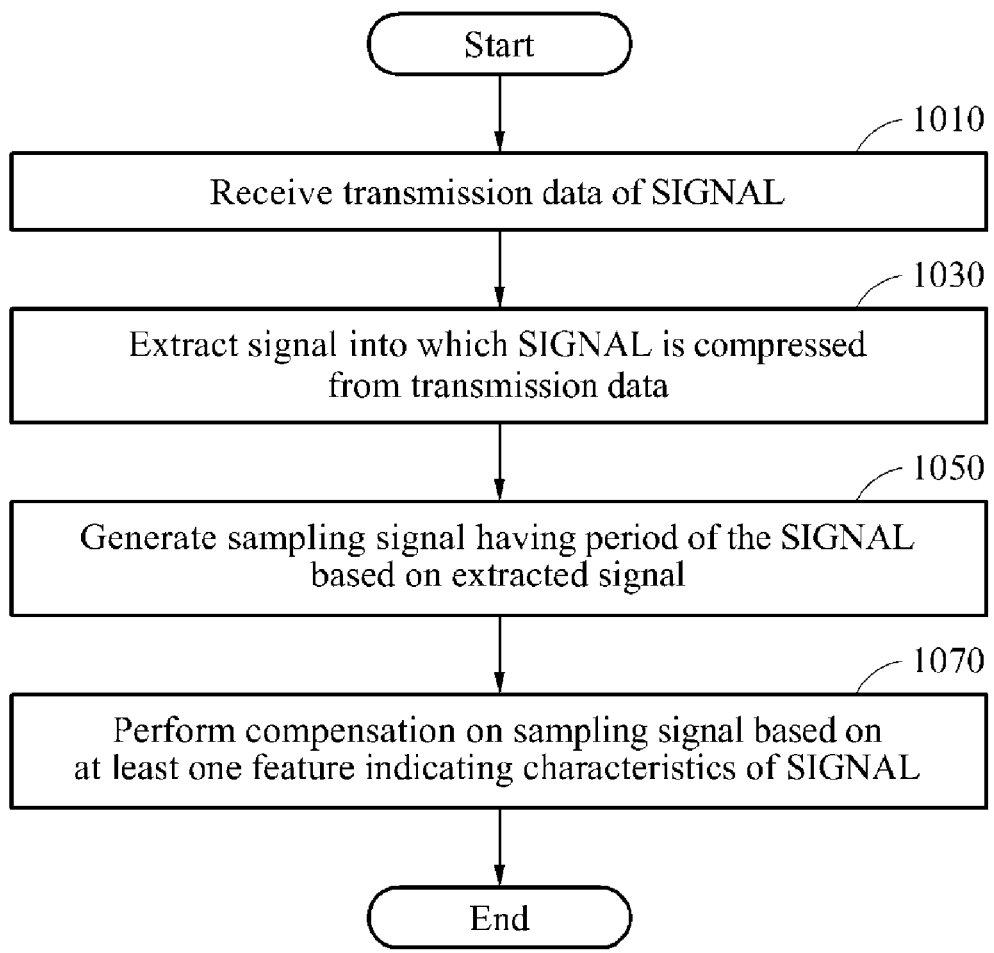
FIG. 10 illustrates an example of a signal recovering method according to example embodiments.

FIG. 10 illustrates an example of a signal recovery method according to example embodiments.

Referring to FIG. 10, in operation 1010, the receiver 210 of the signal recovery device 200 may receive transmission data of SIGNAL from an external device, for example, the signal processing device 100.

In operation 1030, the controller 230 may extract a signal into which the SIGNAL is compressed from the transmission data.

In operation 1050, the controller 230 may generate a sampling signal having a period of the SIGNAL based on the extracted signal.

In operation 1070, the controller 230 may perform compensation on the sampling signal based on at least one feature indicating characteristics of the SIGNAL. In some example embodiments, the controller 230 may extract the at least one feature from the transmission data. In other example embodiments, the controller 230 may estimate the at least one feature.

Figure 11:
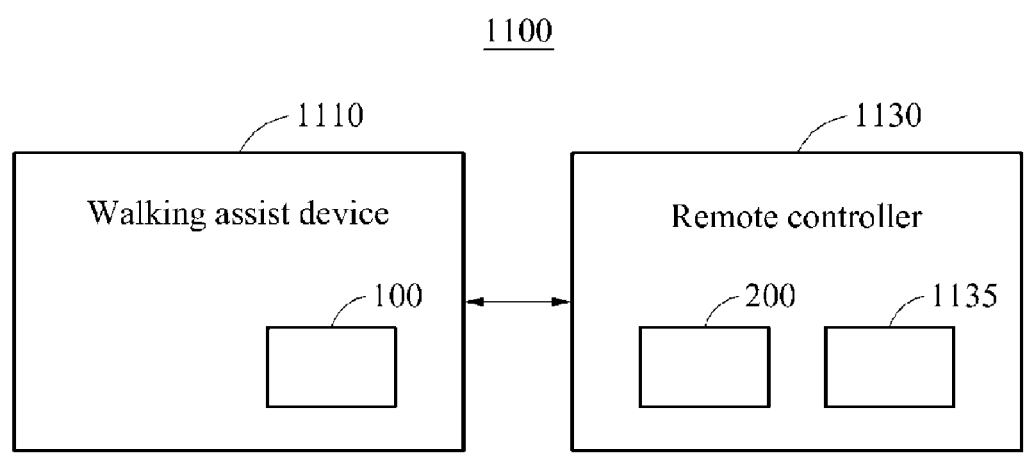
FIG. 11 illustrates another example of an electronic system according to example embodiments.

FIG. 11 illustrates an example of an electronic system according to example embodiments.

Referring to FIG. 11, an electronic system 1100 may be, for example, a walking assist system.

The electronic system 1100 may include a walking assist device 1110 and a remote controller 1130. In this disclosure, the term "walking" may be interchangeably used with the term "gait."

The walking assist device 1110 may include the signal processing device 100 of FIG. 1. The remote controller 1130 may include the signal recovering device 200 of FIG. 1.

The walking assist device 1110 may be worn by a target body, for example, a user, to assist a gait and/or a motion of the user. The target of object may be, for example, a person, an animal, and a robot, and an example of the target body is not limited thereto.

The walking assist device 1110 may assist a gait and/or a motion of, for example, a hand, an upper arm, a lower arm, and the other part of an upper body of the user. Alternatively, the walking assist device 1110 may assist a gait and/or a motion of, for example, a foot, a calf, a thigh, and the other part of a lower body of the user. Thus, the walking assist device 1110 may assist a gait and/or a motion of a part of the user.

The remote controller 1130 may control an overall operation of the walking assist device 1110 in response to an input of the user.

When the user performs a gait with an assistance of the walking assist device 1110, the signal processing device 100 may receive a gait signal sensed by a sensor based on the gait of the user and process the gait signal. The signal processing device 100 may generate transmission data of the gait signal based on at least one feature indicating characteristics of the gait signal and a result of the processing. The signal processing device 100 may transmit the transmission data to the remote controller 1130.

The signal recovering device 200 of the remote controller 1130 may extract a signal into which the gait signal is compressed from the transmission data and recover the gait signal based on the extracted signal and the at least one feature indicating the characteristics of the gait signal.

The remote controller 1130 may further include a display 1135. The display 1135 may display the gait signal recovered by the signal recovering device 200. Thus, the user may verify the gait signal generated through the walking assist device 1110 on the display 1135.

The display 1135 may be implemented as, for example, a touchscreen, a liquid crystal display (LCD), a thin film transistor-liquid crystal display (TFT-LCD), a liquid emitting diode (LED) display, an organic LED (OLED) display, an active matrix OLED (AMOLED) display, and a flexible display.

Figure 12:
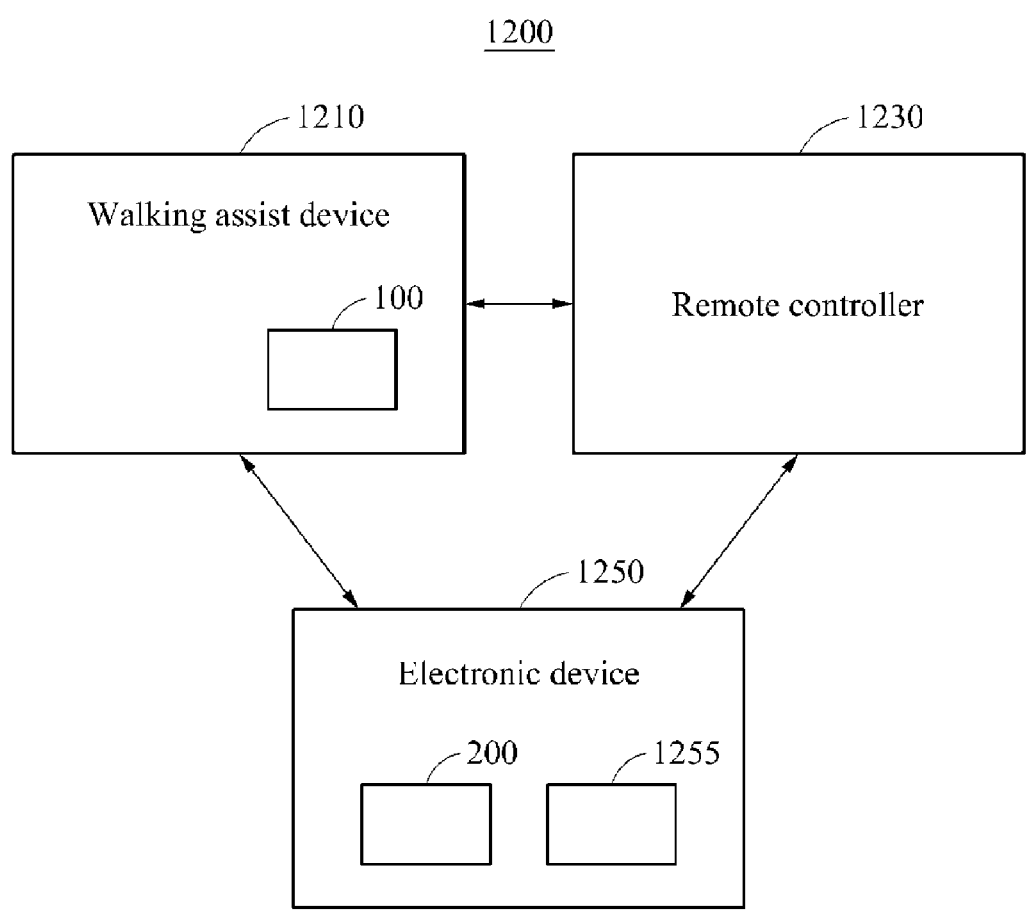
FIG. 12 illustrates still another example of an electronic system according to example embodiments.

FIG. 12 illustrates an example of an electronic system according to example embodiments.

Referring to FIG. 12, the electronic system 1200 may be, for example, a walking assist system.

The electronic system 1200 may include a walking assist device 1210, a remote controller 1230, and an electronic device 1250.

The walking assist device 1210 may include the signal processing device 100 of FIG. 1. The electronic device 1250 may include the signal recovering device 200 of FIG. 1.

Configurations and operations of the walking assist device 1210 and the remote controller 1230 of FIG. 12 may be substantially the same as configurations and operations of the walking assist device 1110 and the remote controller 1130 of FIG. 11.

The electronic device 1250 may communicate with the walking assist device 1210 and/or the remote controller 1230. The electronic device 1250 may be implemented as, for example, a PC, a data server, and a portable electronic device.

The portable electronic device may be implemented as, for example, a laptop computer, a mobile phone, a smartphone, a tablet PC, an MID, a PDA, an EDA, a digital still camera, a digital video camera, a PMP, a PND, a handheld console, an e-book, and a smart device. The smart device may be implemented as, for example, a smart watch and a smart band.

When a user performs a gait with an assistance of the walking assist device 1210, the signal processing device 100 may receive a gait signal sensed by a sensor based on the gait of the user and process the gait signal. The signal processing device 100 may generate transmission data of the gait signal based on at least one feature indicating characteristics of the gait signal and a result of the processing. The signal processing device 100 may transmit the transmission data to the electronic device 1250.

The signal recovering device 200 of the electronic device 1250 may extract a signal into which the gait signal is compressed from the transmission data and recover the gait signal based on the extracted signal and the at least one feature indicating the characteristics of the gait signal.

The electronic device 1250 may further include a display 1255. The display 1255 may display the gait signal recovered by the signal recovering device 200. Thus, the user may verify the gait signal generated through the walking assist device 1210 on the display 1255.

The display 1255 may be implemented as, for example, a touchscreen, an LCD, a TFT-LCD, an LED display, an OLED display, an AMOLED display, and a flexible display.

Example embodiments provide technology for efficiently generating compression data of a signal based on at least one feature indicating characteristics of the signal and a signal into which the signal is compressed.

Example embodiments also provide technology for efficiently recovering an original signal from compression data by compensating for a distortion due to a compression based on at least one feature indicating characteristics of the original signal.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:
1. A signal processing method comprising:
sampling a data signal to generate a sampled signal;
compressing the sampled signal based on a quantization parameter to generate a compressed signal; and
generating transmission data by matching at least one characteristic feature in the data signal and the compressed signal.
2. The signal processing method of claim 1, further comprising:
determining the at least one characteristic feature within the data signal.
3. The signal processing method of claim 1, wherein the at least one characteristic feature includes a start point, an end point, a peak point, and a valley point of the data signal.
4. The signal processing method of claim 1, wherein the data signal indicates a movement of a user.
5. The signal processing method of claim 4, wherein the at least one characteristic feature is based on a gait characteristic of the user.
6. The signal processing method of claim 1, wherein the method further comprises:
appending sampling information associated with the sampling of the data signal to a header of the transmission data.
7. The signal processing method of claim 1, further comprising:
detecting the data signal at one or more intervals determined based on at least one step of a user associated with the data signal.

8. A signal recovering method comprising:
receiving transmission data from an external device;
extracting, from the transmission data, a compressed signal having a data signal detected by the external device therein; and
recovering the data signal based on the compressed signal and at least one characteristic feature of the data signal, the recovering including,
   decompressing the compressed signal based on a quantization parameter to generate a decompressed signal, and
   sampling the decompressed signal based on sampling information included in the transmission data to generate a sampling signal having a same period as the data signal.

9. The signal recovering method of claim 8, wherein the recovering comprises:
performing compensation on the sampling signal based on the at least one characteristic feature.

10. The signal recovering method of claim 8, further comprising:
extracting the at least one characteristic feature from the transmission data.

11. The signal recovering method of claim 8, further comprising:
estimating the at least one characteristic feature based on the transmission data.

12. The signal recovering method of claim 8, wherein the at least one characteristic feature includes at least one of a start point, an end point, a peak point, and a valley point of the data signal.

13. The signal recovering method of claim 8, wherein the data signal indicates a movement of a user.

14. The signal recovering method of claim 13, wherein the at least one characteristic feature is based on a gait characteristic of the user.

15. A signal processing device comprising:
a receiver configured to receive a data signal; and
a controller configured to,
   sample the data signal to generate a sampled signal,
   compress the sampled signal based on a quantization parameter to generate a compressed signal, and
   generate transmission data by matching at least one characteristic feature in the data signal and the compressed signal.

16. The signal processing device of claim 15, wherein the controller is configured to determine the at least one characteristic feature within the data signal.

17. The signal processing device of claim 15, wherein the at least one characteristic feature includes at least one of a start point, an end point, a peak point, and a valley point of the data signal.

18. The signal processing device of claim 15, wherein the data signal indicates a movement of a user.

19. The signal processing device of claim 18, wherein the at least one characteristic feature is based on a gait characteristic of the user.

20. The signal processing device of claim 15, wherein the controller is configured to detect the data signal received by the receiver at one or more intervals determined based on at least one step of a user associated with the data signal.

21. A signal recovering device comprising:
a receiver configured to receive transmission data from an external device; and
a controller configured to,
   extract, from the transmission data, a compressed signal having a data signal detected by the external device therein, and
   recover the data signal based on the compressed signal and at least one characteristic feature of the data signal by decompressing the compressed signal based on a quantization parameter to generate a decompressed signal and sampling the decompressed signal based on sampling information included in the transmission data to generate a sampling signal having a same period as the data signal.

22. The signal recovering device of claim 21, wherein the controller is configured to,
perform compensation on the sampling signal based on at least one characteristic feature of the data signal.

23. The signal recovering device of claim 21, wherein the controller is configured to extract the at least one characteristic feature from the transmission data.

24. The signal recovering device of claim 21, wherein the controller is configured to estimate the at least one characteristic feature based on the transmission data.

25. The signal recovering device of claim 21, wherein at least one the characteristic feature includes at least one of a start point, an end point, a peak point, and a valley point of the data signal.

26. The signal recovering device of claim 21, wherein the data signal indicates a movement of a user.

27. The signal recovering device of claim 26, wherein the at least one characteristic feature is based on a gait characteristic of the user.

* * * * *